Figure 1:
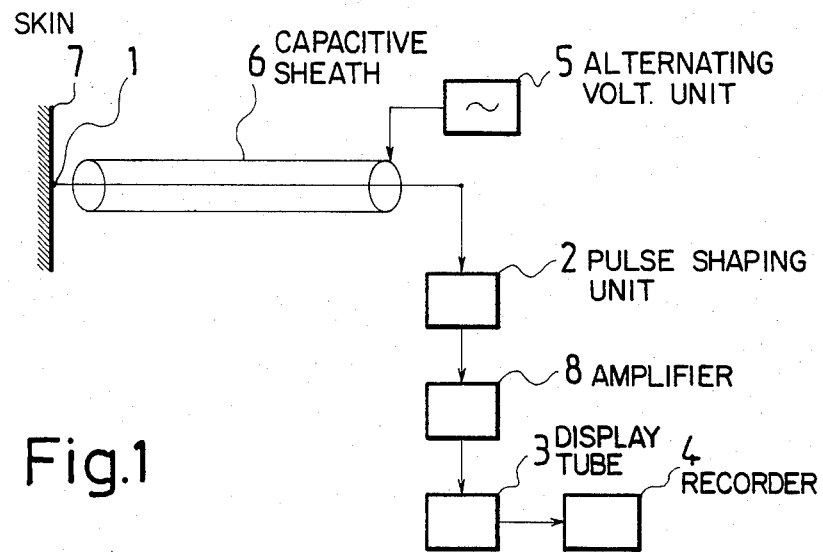

United States Patent [19]
Martio et al.

[11] Patent Number: 4,498,479
[45] Date of Patent: Feb. 12, 1985

[54] ELECTROCARDIOGRAPH (ECG) ELECTRODE TESTING SYSTEM

[75] Inventors: Asko Martio, Espoo; Ilpo Reitmaa, Kaipola; Esa Lautamo, Espoo, all of Finland

[73] Assignee: Kone Oy, Helsinki, Finland

[21] Appl. No.: 391,950

[22] Filed: Jun. 24, 1982

[30] Foreign Application Priority Data

Jun. 24, 1981 [FI] Finland ................................ 811978

[51] Int. Cl.³ ............................................ A61B 17/36
[52] U.S. Cl. ............................. 128/639; 128/303.13; 128/783; 128/421
[58] Field of Search ............... 128/731, 703, 706, 902, 128/696, 639–644, 908, 303.13, 303.14, 419 P, 128/419 R, 421, 422, 783–786

[56] References Cited
U.S. PATENT DOCUMENTS 4,303,073  12/1981  Archibald ..................... 128/303.13

Primary Examiner—K. L. Howell
Assistant Examiner—Steven Falk

[57] ABSTRACT

A system for testing the attachment of an electrocardiograph (ECG) electrode intended to be used in connection with an electrode monitoring the function of the heart, muscles or other organs to indicate detachment of the electrode from its fixing base, said electrode being provided with voltage monitoring apparatus. The electrode comprises a capacitive sheath insulated from the electrode and from its fixing base and an alternating voltage source arranged to supply a signal voltage to the sheath so that on detachment of the electrode from its fixing base immediately an alternating voltage is induced from the sheath to the electrode.

4 Claims, 2 Drawing Figures

ELECTROCARDIOGRAPH (ECG) ELECTRODE TESTING SYSTEM

BACKGROUND OF INVENTION

The present invention concerns a system for testing the attachment of an electrocardiograph (ECG) electrode, this means being intended for use in connection with an electrode monitoring the function of heart, muscles or other organs, to indicate the event of the electrode's detachment from its fixing base, said electrode having been provided with a voltage monitoring apparatus.

ECG electrodes and their ancillaries are nowadays extensively used in examinations of the heart or brain, or in general when observing the electrical voltages and voltage changes on a patient's organs. Such monitoring is accomplished with the aid of said ECG electrode, which has been attached to the body part under observation and connected to amplifier, pulse shaper, display and other requisite units, and possibly to a recorder. Attachment of the electrode on the skin is usually done with the aid of adhesive tape or any other binding element, and using a compound which improves the contact between skin and electrode.

These means of prior art have their drawbacks, however. Difficulties are in particular experienced in ascertaining the continuous attachment of the electrode to the skin, because accidental detachment is not readily noticed. To this end a testing apparatus has been used in connection with an ECG electrode, consisting of a separate lead and of a signal voltage source including a current intensity meter indicating the signal current passing between the electrode and the human subject. When this current is broken, one knows that the electrode has become detached. However, this procedure implies the use of an extra lead attached to the patient, this lead requiring a fixing of its own and thus even further complicating the situation, as well as a signal voltage, which then even introduces the risk of electric shock to the patient.

SUMMARY OF INVENTION

The object of the present invention is to eliminate the drawbacks mentioned above. The invention is characterized in that the electrode comprises a capacitive sheath, insulated from the electrode and from its fixing base, and an alternating voltage source, arranged to supply a signal voltage to the sheath. In such an arrangement, the capacitance of the sheath causes a signal voltage to be induced on the electrode as soon as the electrode comes off its fixing base. While the electrode is attached to its base, the capacitance of the human body, which is substantially higher than that of the sheath, prevents such a voltage from being induced. It is thus understood that any detachment of the electrode from its fixing base is immediately visible in the display, which then begins to display the signal voltage.

Thus, the testing means or system of the invention is simple as to its construction, yet reliable in operation all the same. It is also a fact that no detriment or danger whatsoever is caused to the patient by the testing means of the invention. Furthermore, the invention is easy to apply in connection with ECG electrodes in present use; the measuring pick-up and cable with its sheath are eminently usable as taught by this invention.

DESCRIPTION OF INVENTION

The invention is described in detail in the following with the aid of an embodiment example with reference being made to the attached drawing, wherein:

FIG. 1 presents, in a simplified principle diagram, an ECG electrode with its ancillary equipment attached on the skin of a human and provided with a testing means according to the invention.

Figure 2:

FIG. 2 shows a typical signal voltage used in the testing means of the invention.

The testing system of the invention for an ECG electrode 1 is intended to be used in connection with an electrode monitoring electrically the function of the heart, muscles or other organs to indicate the event of detachment of the electrode from its fixing base 7, which is usually the human skin. The ECG electrode 1 belongs as a part to the observation apparatus by which the electrical monitoring of said organs takes place. The observation apparatus usually comprises a pulse shaping unit 2, an amplifier means 8 and a display unit, such as a display tube 3 or a recorder 4, by the aid of which the ultimate monitoring of the voltage is accomplished.

As taught by the invention, the ECG electrode 1 comprises a conductive and capacitive sheath 6 insulated from the electrode and from its fixing base, and an alternating voltage source 5, arranged to supply a signal voltage to the sheath 6. When using the means, the electrode 1 is attached on the human skin fixing base 7, e.g. with the aid of electrode compound and adhesive tape, and the observation apparatus comprising the amplifier means 8 and the display tube 3 and recorder 4 is switched on. Moreover, a signal voltage is supplied from the alternating voltage source 5 to the sheath 6 of the electrode 1. With the electrode 1 attached to the human skin 7, the capacitance of the person prevents the alternating voltage supplied to the sheath 6 from being induced to the electrode 1, and nothing but the voltage variations caused by the skin 7 are visible in the display 3 and recorder 4. When the electrode 1 becomes detached from the skin 7 or the contact between them is otherwise broken, an alternating voltage will immediately be induced from the sheath 6 to the electrode 1. This alternating voltage induced in the electrode 1 is immediately visible in the display 3 and recorder 4 as a signal voltage, for instance in the shape shown in FIG. 2, which at the same time differs clearly from the voltage produced by the organ under examination. It follows that any detachment of the electrode 1 from its fixing base 7 is most readily observed by the simple apparatus of the present invention.

Naturally, the invention is not confined to the embodiment example presented, but its application may vary for instance within the scope of the claims following below. For instance, the design of the sheath 6 may vary even considerably and it may consist e.g. of the sheath conductor of a coaxial cable, of a separate conductor placed beside the attachment lead of the electrode 1, or in general of any conductor having a capacitive effect. Likewise, the design of the voltage source 5 may vary and it may consist of any type, known in itself, of apparatus intended for producing alternating voltage, or a periodically changing voltage in general.

We claim:

1. A system for testing the attachment of an ECG electrode intended to be used in connection with an electrode monitoring the function of the heart, muscles or other human organs to indicate detachment of the electrode from its fixing base on the human skin, said system comprising:

an ECG electrode having a fixing base for connecting the electrode to the skin of a patient, wherein the electrode comprises a conductive capacitive sheath electrically insulated from the electrode and from said fixing base;

an alternating voltage source supplying a signal voltage to the sheath; and voltage monitoring and display apparatus electrically connected to said electrode, so that on any detachment of the electrode from said fixing base an alternating voltage from said voltage source is immediately induced from the sheath to the electrode and is displayed in said voltage monitoring and display apparatus.

2. The electrode attachment testing system of claim 1, wherein said voltage monitoring and display apparatus includes a pulse shaper unit, an amplifier, and a display tube all functionally interconnected to each other.

3. The electrode attachment testing system of claim 1, wherein said voltage monitoring and display apparatus includes a recorder unit connected to the display tube.

4. A system for testing the attachment of an ECG electrode intended to be used in connection with an electrode monitoring the function of the heart, muscles and other human organs to indicate detachment of the electrode from its fixing base on the human skin, said system comprising:

(a) an ECG electrode having a fixing base for connecting the electrode to human skin, wherein the electrode comprises a conductive capacitive sheath electrically insulated from the electrode and from said fixing base;

(b) an alternating voltage source supplying a signal voltage to the sheath; and (c) voltage monitoring and display apparatus including a pulse shaper unit, an amplifier, a display tube all electrically and functionally interconnected to each other, and a recorder unit electrically connected to said display tube, whereby upon any detachment of said electrode from said fixing base an alternating voltage from said voltage source is immediately induced from said sheath to the electrode, and the voltage is displayed on said display tube and said recorder unit.

* * * * *